(12) United States Patent
Flanagan (10) Patent No.: US 7,786,406 B2
(45) Date of Patent: *Aug. 31, 2010

(54) LASER STENT CUTTING

(75) Inventor: Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 558 days.

This patent is subject to a terminal disclaimer.

(21) Appl. No.: 10/784,549

(22) Filed: Feb. 23, 2004

(65) Prior Publication Data

US 2004/0226922 A1    Nov. 18, 2004

Related U.S. Application Data

(63) Continuation of application No. 10/301,984, filed on Nov. 22, 2002, now Pat. No. 6,696,667.

(51) Int. Cl.
*B23K 268/38* (2006.01)

(52) U.S. Cl. .............................. 219/121.72; 219/121.7; 219/121.71

(58) Field of Classification Search ............. 219/121.7, 219/121.71, 121.72, 121.6, 121.67, 121.68, 219/121.69, 121.74, 121.75
See application file for complete search history.

(56) References Cited

U.S. PATENT DOCUMENTS

| | | | | |
|---|---|---|---|---|
| 4,456,811 A * | 6/1984 | Hella et al. | ............ | 219/121.85 |
| 4,695,132 A * | 9/1987 | Sakuma | ...................... | 359/662 |
| 5,109,149 A * | 4/1992 | Leung | .................. | 219/121.69 |
| 5,486,694 A * | 1/1996 | Harris | ........................ | 250/236 |
| 5,514,145 A | 5/1996 | Durham et al. | ............... | 606/96 |
| 5,620,618 A * | 4/1997 | Freedenberg et al. | .. | 219/121.74 |
| 5,759,192 A | 6/1998 | Saunders | ..................... | 606/194 |
| 5,780,807 A | 7/1998 | Saunders | ............... | 219/121.71 |
| 5,835,253 A * | 11/1998 | Paoli et al. | .................. | 359/216 |
| 5,852,277 A | 12/1998 | Gustafson | ............. | 219/121.67 |
| 5,994,667 A | 11/1999 | Merdan et al. | ......... | 219/121.67 |
| 6,034,349 A | 3/2000 | Ota | ........................ | 219/121.73 |
| 6,131,266 A | 10/2000 | Saunders | ..................... | 29/557 |
| 6,197,048 B1 | 3/2001 | Richter | ..................... | 623/1.15 |
| 6,521,865 B1 | 2/2003 | Jones et al. | ............. | 219/121.72 |
| 6,563,080 B2 * | 5/2003 | Shapovalov et al. | .... | 219/121.72 |
| 6,612,012 B2 | 9/2003 | Mitelberg et al. | ............. | 29/447 |
| 6,653,593 B2 * | 11/2003 | Lizotte et al. | ............ | 219/121.7 |
| 6,696,667 B1 * | 2/2004 | Flanagan | ............... | 219/121.72 |
| 6,705,736 B1 * | 3/2004 | Pressler | ..................... | 359/853 |
| 2002/0108937 A1 | 8/2002 | Shapovalov et al. | | |

FOREIGN PATENT DOCUMENTS

GB    2244851    * 11/1991

OTHER PUBLICATIONS

Definition Extract, Dictionary.com Unabridged Based on the Random House Dictionary, © Random House, Inc. 2009.*

* cited by examiner

*Primary Examiner*—Roy King
*Assistant Examiner*—Michael Aboagye
(74) *Attorney, Agent, or Firm*—Mayer & Williams PC; David B. Bonham; Stuart H. Mayer

(57) ABSTRACT

A stent may be manufactured by providing a tube having a longitudinal axis therethrough, providing a stationary source of laser radiation, generating a beam of laser radiation using the source of laser radiation, and cutting a desired pattern into the tube by scanning the beam over a desired region of the tube.

17 Claims, 8 Drawing Sheets

Fig. 1
PRIOR ART

LINEAR MOTION AXIS

LASER STENT CUTTING

STATEMENT OF RELATED APPLICATION

This is a continuation of U.S. patent application Ser. No. 10/301,984, filed Nov. 22, 2002, entitled "Improved Laser Stent Cutting," now U.S. Pat. No. 6,696,667.

BACKGROUND OF THE INVENTION

Laser cutting of stents has been disclosed in a number of patents including U.S. Pat. Nos. 5,514,154, 5,759,192, 6,131,266 and 6,197,048 and is the preferred technology for stent manufacture in the medical device industry. The conventional approach is to move a hollow tube of metal such as stainless steel under a stationary laser beam. Although the laser is capable of a very rapid cutting speed, the cutting speed of this approach is limited by the speed of the motion drives and in particular the speed of the rotational motor drive.

Figure 1:
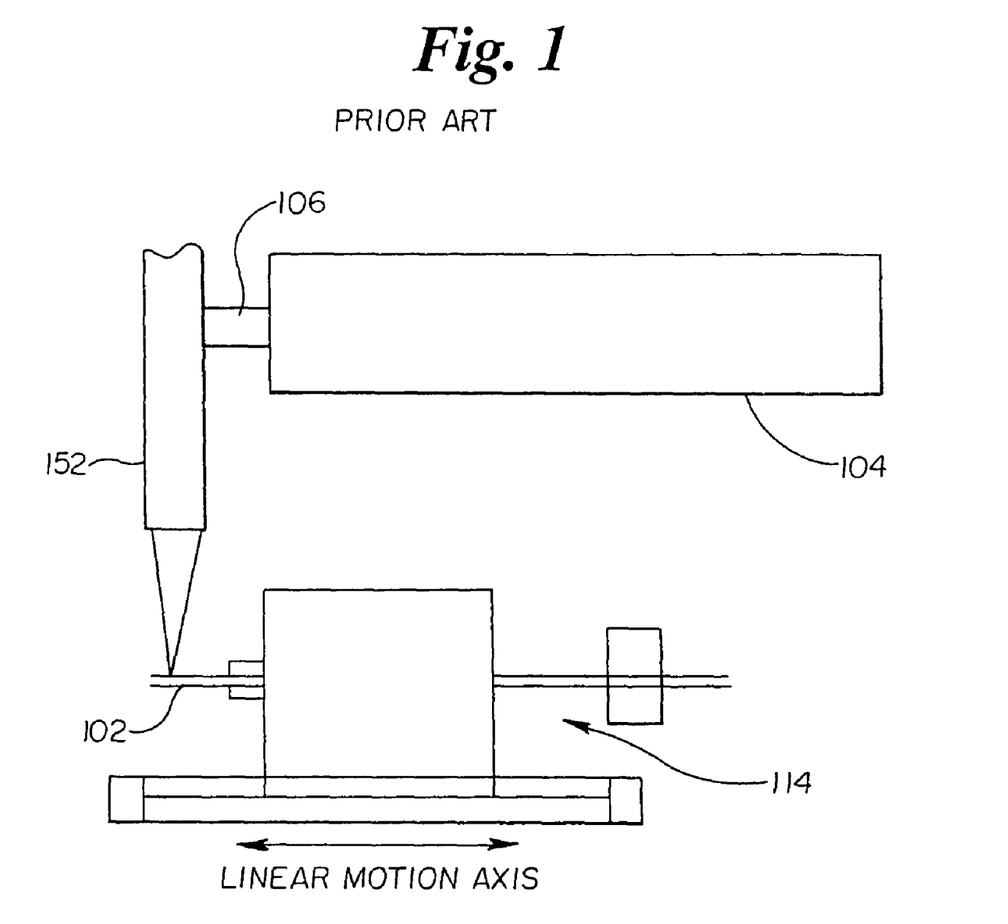
FIG. 1 is a schematic illustration of a prior art apparatus for cutting a stent.

A typical laser arrangement is shown in FIG. 1. Laser 102 produces a beam 106 which is conditioned as necessary via optical unit 104 and focused into a spot beam which is impinged against hollow tube 108. Hollow tube 108 may be rotated via rotational motor drive 110 and linearly translated via linear motion drive 112.

The conventional laser for cutting is a pulsed Nd:YAG laser which has a pulse duration in the range of approximately 0.1 to 20 milliseconds. This is a long pulse time for cutting and characteristically produces a relatively large melt zone and heat affected zone (HAZ) on the metal. The conventional laser cutting process typically results in the formation of melt dross on the inside edge of the cut tube. This dross must be cleaned off in subsequent processes.

Non-uniformities in the material such as differences in wall thickness create different heat rises in the material and lead to variations in cut quality. Laser parameters have to be re-tuned for optimum cutting for tubes with slightly different wall thicknesses adding to the downtime of the process and reducing the yield.

As the industry moves toward the use of stents having slightly different strut thickness at different positions within the stent, there remains a need for novel methods of rapidly cutting stents from tubes. There also remains a need for developing novel methods of cutting stents from tubes with smaller melt regions and smaller heat affected zone regions than is presently available.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the instant invention is directed to a method of manufacturing a stent. The method involves cutting a desired pattern in a tube and comprises the steps of providing a tube having a longitudinal axis therethrough, providing a stationary source of laser radiation, generating a beam of laser radiation using the source of laser radiation, and cutting a desired pattern into the tube by scanning the beam over a desired region of the tube.

In some embodiments the laser is scanned or directed over the cutting path multiple times until it cuts through the wall of the metal completely. The laser parameters are set such that on each pass each sequential laser pulse overlaps by a certain amount on the material surface and a small amount of material thereby is removed creating a channel in the material in the desired pattern. Each subsequent pass of the laser creates a deeper channel until finally the last pass of the laser breaks through the bottom surface of the material. This approach has the advantage of minimizing the amount of energy being absorbed into the work piece at one location. This is because after the laser has passed a particular location the heat created in the material dissipates, and also the vaporized material dissipates before the laser returns for its next pass. Because the material vapor dissipates before the next pass of the laser there are no plasma absorption effects as seen in normal multiple cutting (such as when metal vapor is present in the channel or hole part of the laser energy is absorbed creating a hot plasma that in turn causes a larger heat affected zone and recast layer). The multiple scan approach leads to reduced heat affected zone (HAZ), recast material, and slag. Finer details can therefore be cut into the stent shape. This approach is suited to the galvanometer scanning method because of the high speed of scanning.

During the cutting step, the beam may also be deflected about a first axis and about a second axis where the first and second axes are orthogonal to one another and orthogonal to the longitudinal axis of the tube. The beam may be deflected using a single mirror which may be pivoted about the first and second axes. Typically, during the cutting step, the beam is scanned in a circumferential direction by pivoting a first scanning mirror in the path of the beam about a first axis and by pivoting a second mirror in the path of the beam about a second axis, the first and second axes orthogonal to one another and orthogonal to the longitudinal axis of the tube, the first and second mirrors redirecting the beam.

Desirably, the tube is translated in a longitudinal direction relative to the beam during the cutting step.

Desirably, a pulsed laser beam may be used, with the laser pulses having a duration of 100 ns or less. Even more desirably, laser pulses having a duration of 100 ps or less may be used.

Where a pulsed laser is used, the laser beam desirably, may be characterized by a repetition rate of 25 kHz or greater. Desirably, the laser beam is characterized by a pulse power of $10^8$ W/cm$^2$ or greater.

Typically, the laser beam will have a wavelength of 600 nm or less and, desirably, 250 nm or less.

Optionally, the method may further comprise the step of polishing the stent after the cutting step.

In another embodiment, the instant invention is directed to a method of providing one or more openings in a tube for use in manufacturing a medical device. The method involves cutting a desired pattern in a tube and comprises the steps of providing a tube having a longitudinal axis therethrough, providing a stationary source of laser radiation, generating a beam of laser radiation using the source of laser radiation, and cutting a desired pattern into the tube by scanning the beam over a desired region of the tube. The medical device desirably is a stent, vena cava filter or catheter. In the case of a catheter, the pattern is desirably cut into a catheter tube, catheter sheath or catheter bumper.

Additional details and/or embodiments of the invention are discussed below.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the instant invention is directed to a method of manufacturing a stent. The method involves cutting a desired pattern in a tube and comprises the steps of providing a tube having a longitudinal axis therethrough, providing a stationary source of laser radiation, generating a beam of laser radiation using the source of laser radiation, and cutting a desired pattern into the tube by scanning the beam over a desired region of the tube to remove portions of the tube in the desired pattern of the stent and leaving portions of the tube which are to form the stent.

The tube to be cut may be made of suitable biocompatible material such as stainless steel. For example, the tube may be stainless steel of alloy type 316LS. Other grades of stainless steel, and other metals or materials may also be used.

The tube will typically have an outer diameter of about 0.08 inches or less in the unexpanded state and is expandable to diameters of 0.12 inches Or more. The wall thickness of the tube is desirably 0.01 inches thick or less.

Figure 2:
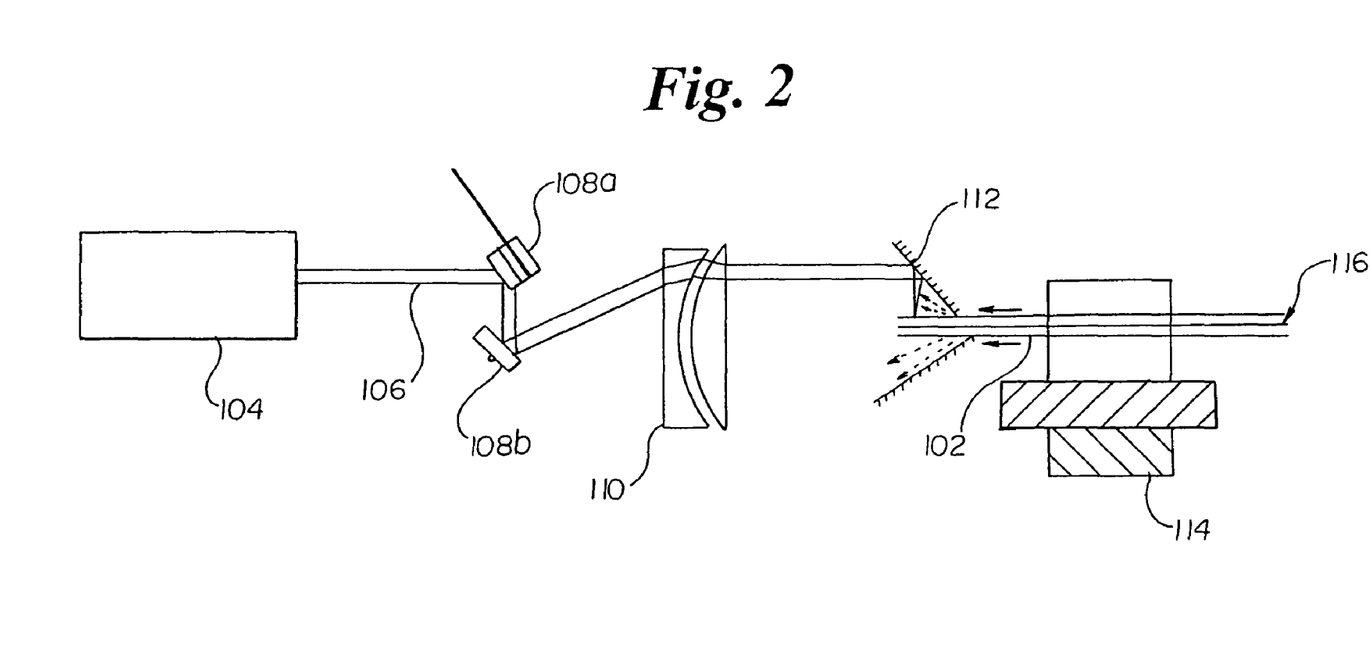
FIG. 2 is a schematic illustration of an inventive laser scanning system for manufacturing a stent.

As shown in FIG. 2, a beam 106 of laser radiation is output from laser source 104. Beam 106 is scanned via the use of an x-y scanning galvanometer using mirrors 108a and 108b. Mirrors 108a and 108b may be controlled by any suitable controller. Beam 106 is then focused via flat field telecentric (f-theta) lens 110 onto a flat focal plane and redirected via a conical mirror 112 to tube 102 in order to cut a desired pattern in the tube. Tube 102 is held in holder 114. Holder 114 is capable of moving the tube in a longitudinal direction. Desirably, tube 102 is disposed about mandril 116. Mandril 116 prevents the laser beam from cutting the opposite inside wall of the tube. The mandril also supports the tube and may reduce or prevent distortion of the tube during the cutting process.

Figure 3:
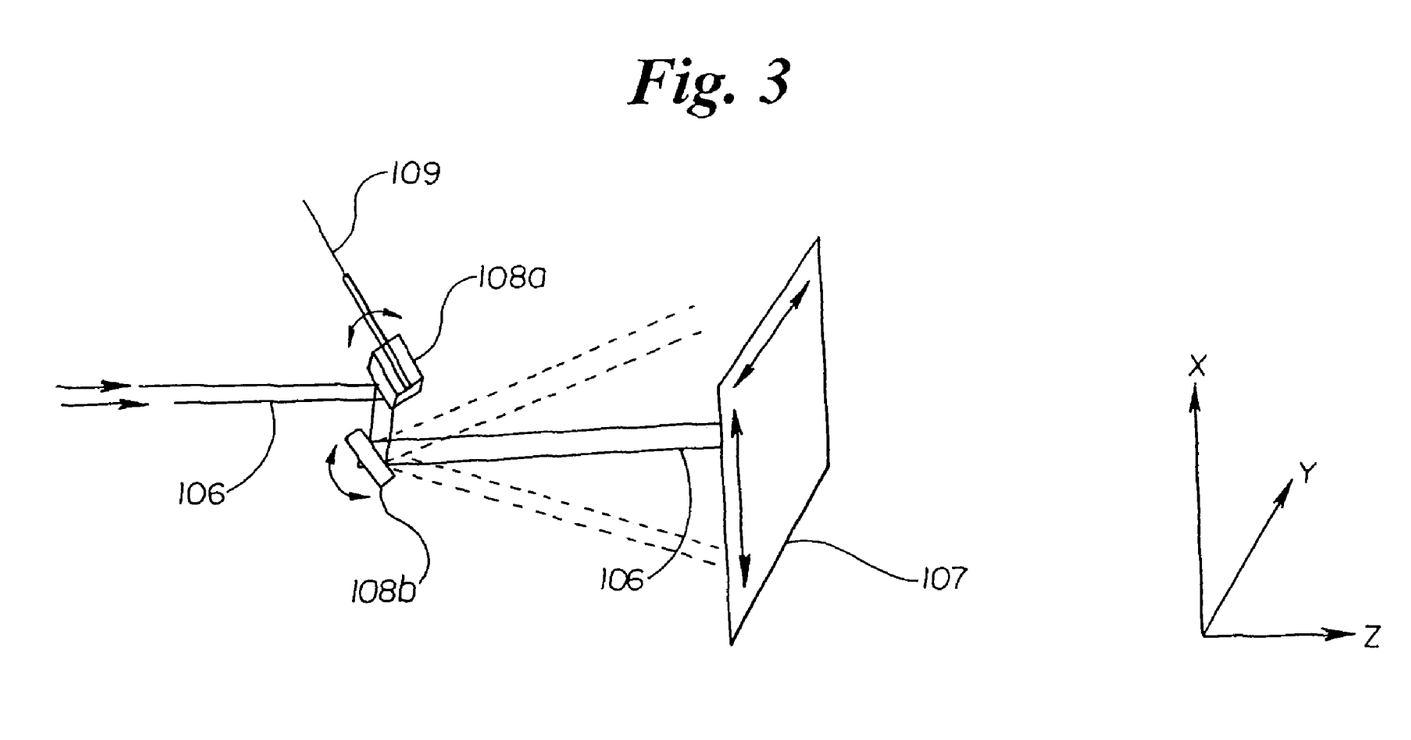
FIG. 3 is a schematic illustration of a portion of an inventive laser scanning system.

The operation of the x-y scanning galvanometer is shown in greater detail in FIG. 3. Mirror 108a may rotate about a first, x, axis 109 and mirror 108b may rotate about a second, y axis shown extending into the plane of the figure. The x and the y axes are at right angles to one another. As the mirrors rotate about their respective axes, beam 106 may be redirected as desired in the x-y plane.

Figure 4:
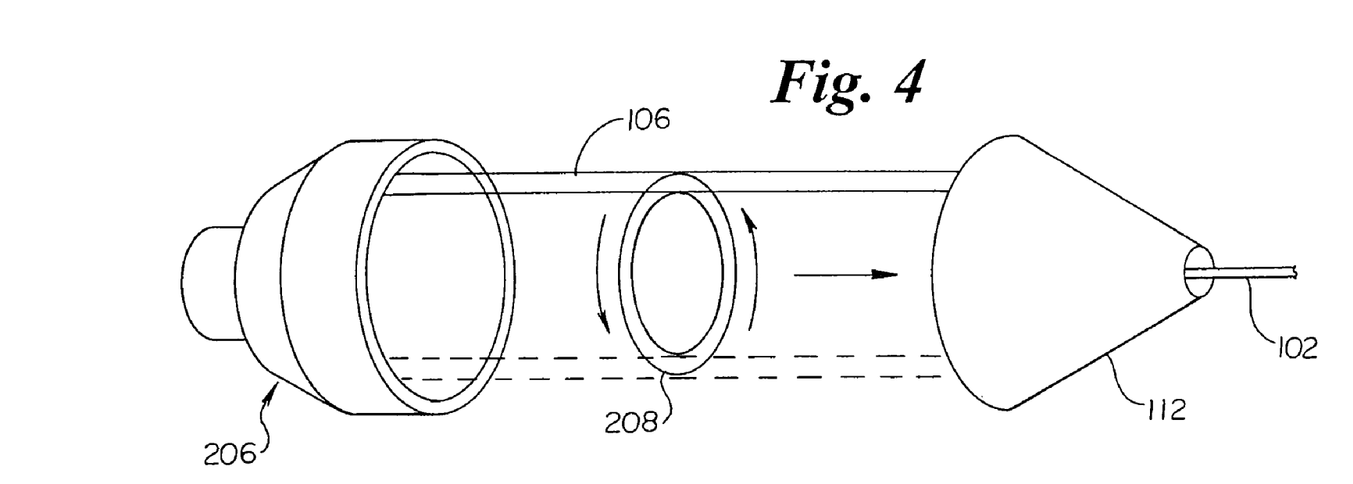
FIG. 4 is a schematic illustration of another portion of an inventive laser scanning system.

The scanning of beam 106 is shown in detail in FIG. 4. Beam 106 is scanned via the x-y galvanometer and focused via the flat field lens, shown as an assembly at 206. In at least one embodiment the assembly 206 comprises a flat field or f-theta telecentric lens. Unlike a prior lenses which provide a curved focal plane or in the case of a non-telecentric flat field lens, a flat focal plane wherein the beam is not incident to the focal plane at 90 degrees over the entire scan area, a flat field or f-theta telecentric lens provides scanning such that the beam 106 is incident to the focal plane at 90 degrees over the entire scan area, as a result the lens provides a substantially flat focal plane.

Figure 5:
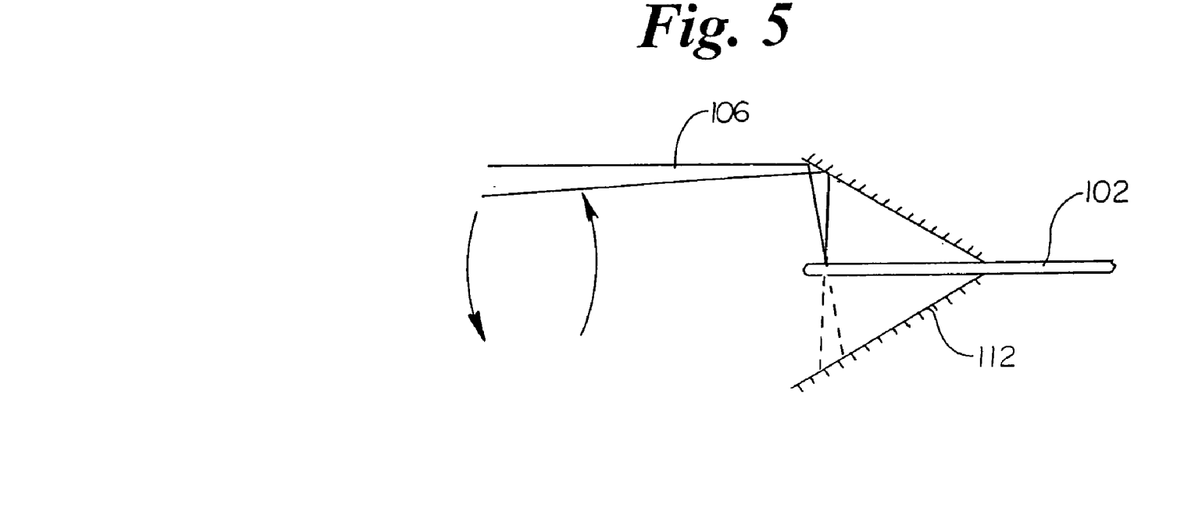
FIG. 5 illustrates a beam scanned about the circumference of a tube.

The mirrors may be controlled to scan the beam in an annulus 208. Upon redirection via conical mirror 112, such as is shown in FIGS. 4 and 5, beam 106 may be scanned about the circumference of tube 102. It is noted that conical mirror 112 has a hole through its apex for receiving tube 102 therethrough. Because a conical mirror is used, the distance between the tube and f-theta lens remains the same around the circumference. Also, because the focal plane is flat as a result of using the f-theta lens, the laser will have the same spot size around the circumference.

By scanning the laser in a desired pattern using the scanning galvanometer, the laser spot may impinge the tube in a desired pattern and cut a desired pattern into the tube. The scanning galvanometer may be controlled using a suitable controller, as known in the art.

In some embodiments of the invention including the embodiment of FIG. 2, the tube may be held stationary and the focal point of the beam moved longitudinally.

Figure 6:
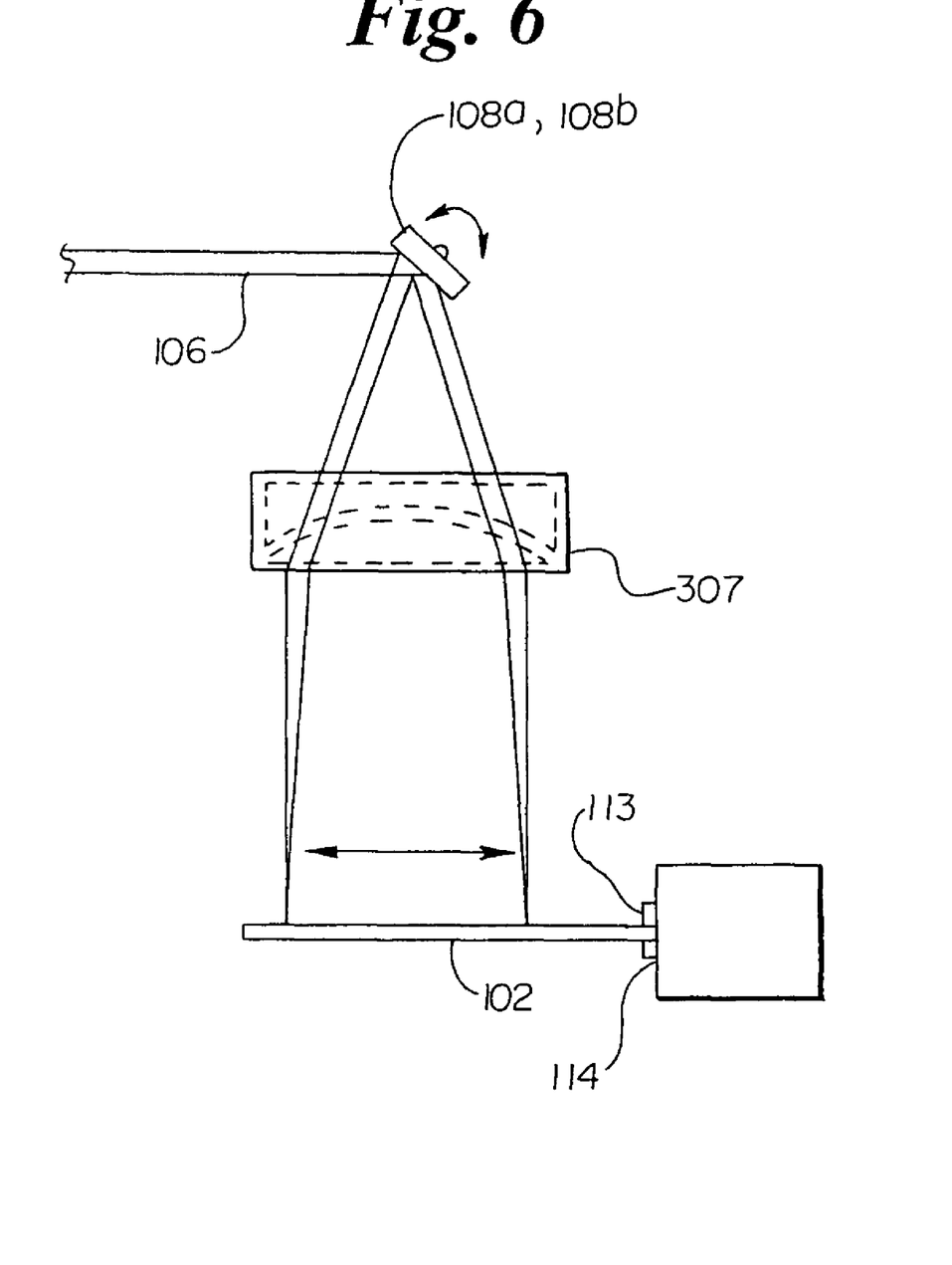
FIG. 6 is a schematic illustration of a portion of an inventive laser scanning system.

Another approach for improved delivery of the laser beam 106 to the tube material 102 is to use scanning galvanometer mirrors 108a/108b with a flat field telecentric lens 307, such as is described above in relation to assembly 206 of FIG. 4, and a rotation device such as a holder 114 having a rotary axis 113 capable of rotating the tube 102 such as is shown in FIG. 6. In the embodiment shown, scanning along a line is only required, therefore only one scanning mirror is required. The lens 307 can thus be reduced to a linear scanning flat field telecentric lens. The tube 102 is rotated about the rotary axis 113 and the beam 106 is scanned axially along the surface of the stent. The stent can be cut in this way using two modes:

The first mode is to continually rotate the tube 102 in one direction. The laser beam 106 is scanned in a line along the top surface of the tube and switched on and off as required wherever it is required to cut the stent pattern.

The second mode is to cut by moving the rotation axis 113 clockwise and counter clockwise and the laser beam 106 scanned along the axis 113 following the stent pattern. Thus the axial (longitudinal) movement is performed by the scanning mirror moving the beam 106. Thus, the holder 114 is not required to provide axial movement to the tube 102.

Figure 7:
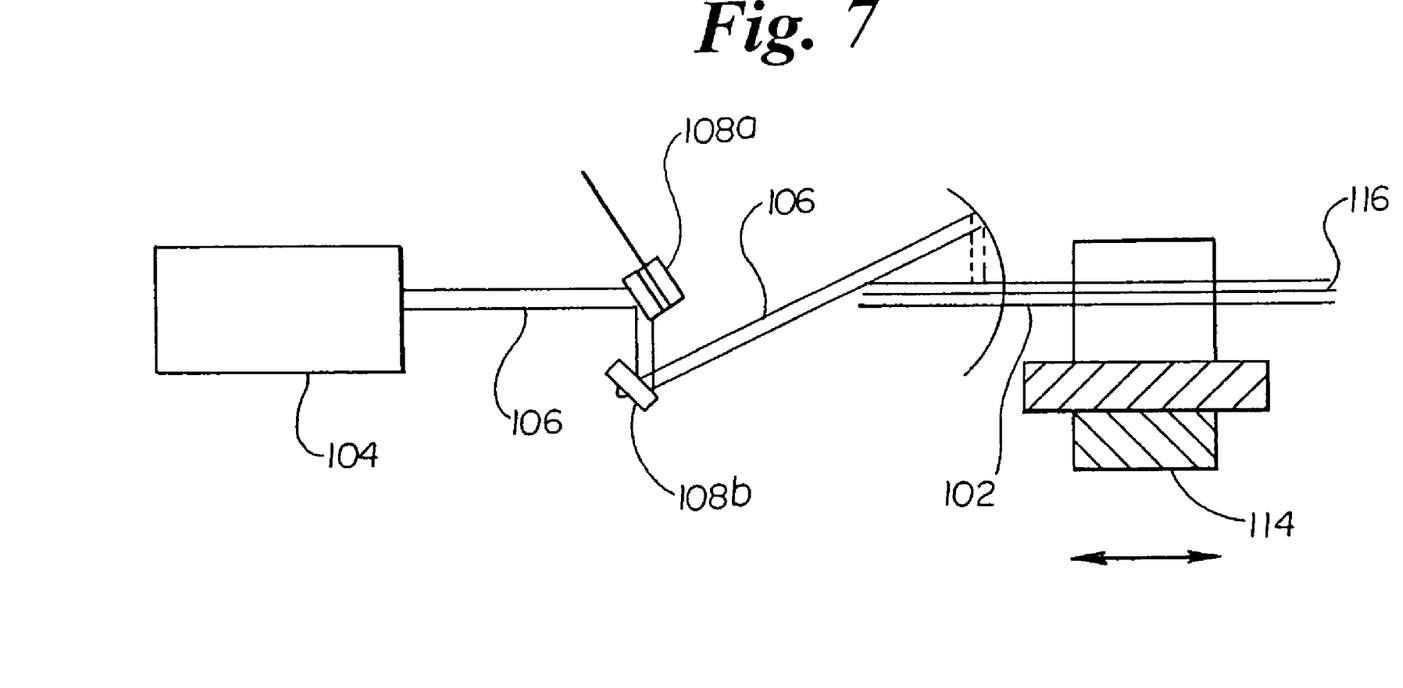
FIG. 7 is a schematic illustration of a portion of another inventive laser scanning system.

In some embodiments of the invention, as discussed above, a holder capable of moving the tube longitudinally relative to the beam may be used. In one such embodiment, a scanning galvanometer is used in conjunction with a parabolic mirror to focus the beam onto the tube. As shown in FIG. 7, beam 106, after exiting scanning galvanometer mirrors 108a and 108b, is directed via elliptical mirror toward tube 102. The beam may be scanned about the circumference of the tube. Holder 114 is moved longitudinally in order to move the tube in a longitudinal direction relative to the beam.

During the cutting step, the beam may also be deflected about a first axis and about a second axis where the first and second axes are orthogonal to one another and orthogonal to the longitudinal axis of the tube. The beam may be deflected using a single mirror which may be pivoted about the first and second axes. Typically, during the cutting step, the beam is scanned in a circumferential direction by pivoting a first scanning mirror in the path of the beam about a first axis and by pivoting a second mirror in the path of the beam about a second axis, the first and second axes orthogonal to one another and orthogonal to the longitudinal axis of the tube, the first and second mirrors redirecting the beam.

Desirably, a pulsed laser beam may be used, with the laser pulses having a duration of 100 ns or less. Even more desirably, laser pulses having a duration of 100 ps or less may be used. The laser beam will typically have a pulse power of $10^8$ $W/cm^2$ or greater.

The laser pulse repetition frequency should be fast enough to allow the required number of pulses to be incident on any given spot on the tube to enable cutting, for any chosen scanning speed. The laser beam desirably will be characterized by a repetition rate of 25 kHz or greater.

Figure 8:
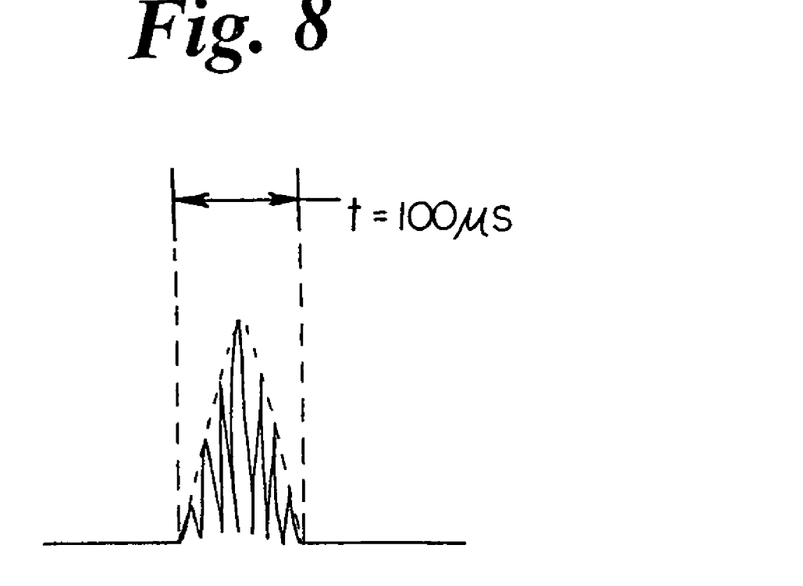
FIGS. 8 and 9 show pulses that may be used in the inventive methods of manufacturing stents.
Figure 9:
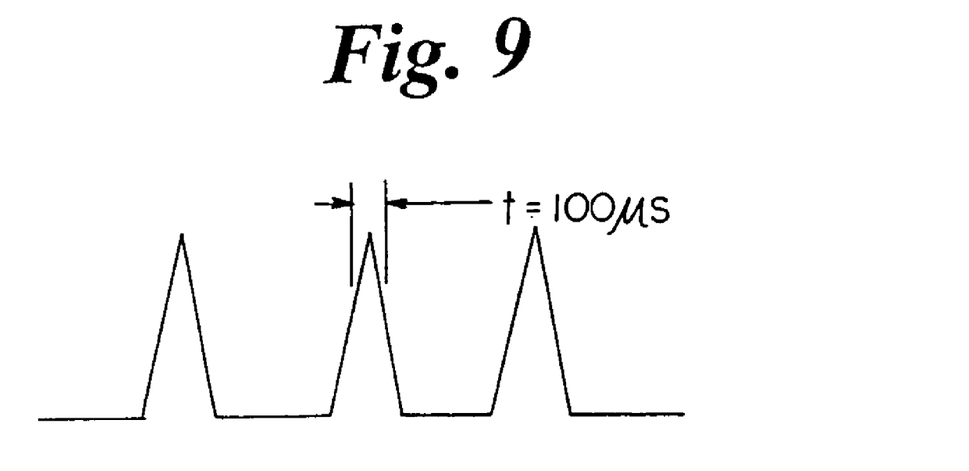

Examples of pulses which may be used are shown in FIGS. 8 and 9.

The laser wavelength desirably will be as short as possible and will typically range from green to ultraviolet wavelengths. Wavelengths of 600 nm or less and, desirably, 355 nm or less may be used. The precise choice of wavelength will depend oh the material being cut.

Without being bound by theory, it is believed that these conditions will enable the cutting mechanism to occur predominately, if not completely by vaporization and ablation rather than via the melting and vaporization of conventional processes.

Suitable lasers for use in the inventive methods include pulsed Nd:YAG lasers. The laser may optionally be diode or flash-lamp pumped with Q-switching, mode locking and frequency multiplication abilities. Other suitable lasers include lasers with Nd doped crystals, copper vapor lasers, excimer lasers and femtosecond lasers.

The cutting process may desirably be monitored and controlled using appropriate sensors to measure various characteristics of the process. The sensors may measure process parameters such as sound, particle emission, reflected laser radiation, emitted radiation from ultraviolet to infrared and the direction of emitted radiation. The measurement may be analyzed by computer software which can automatically adjust the laser parameters to maintain optimal cutting conditions. Suitable algorithms for monitoring and controlling the cutting process include simple PID (proportional, integral differential) programs, fuzzy logic based programs and neural network based programs.

Figure 10:
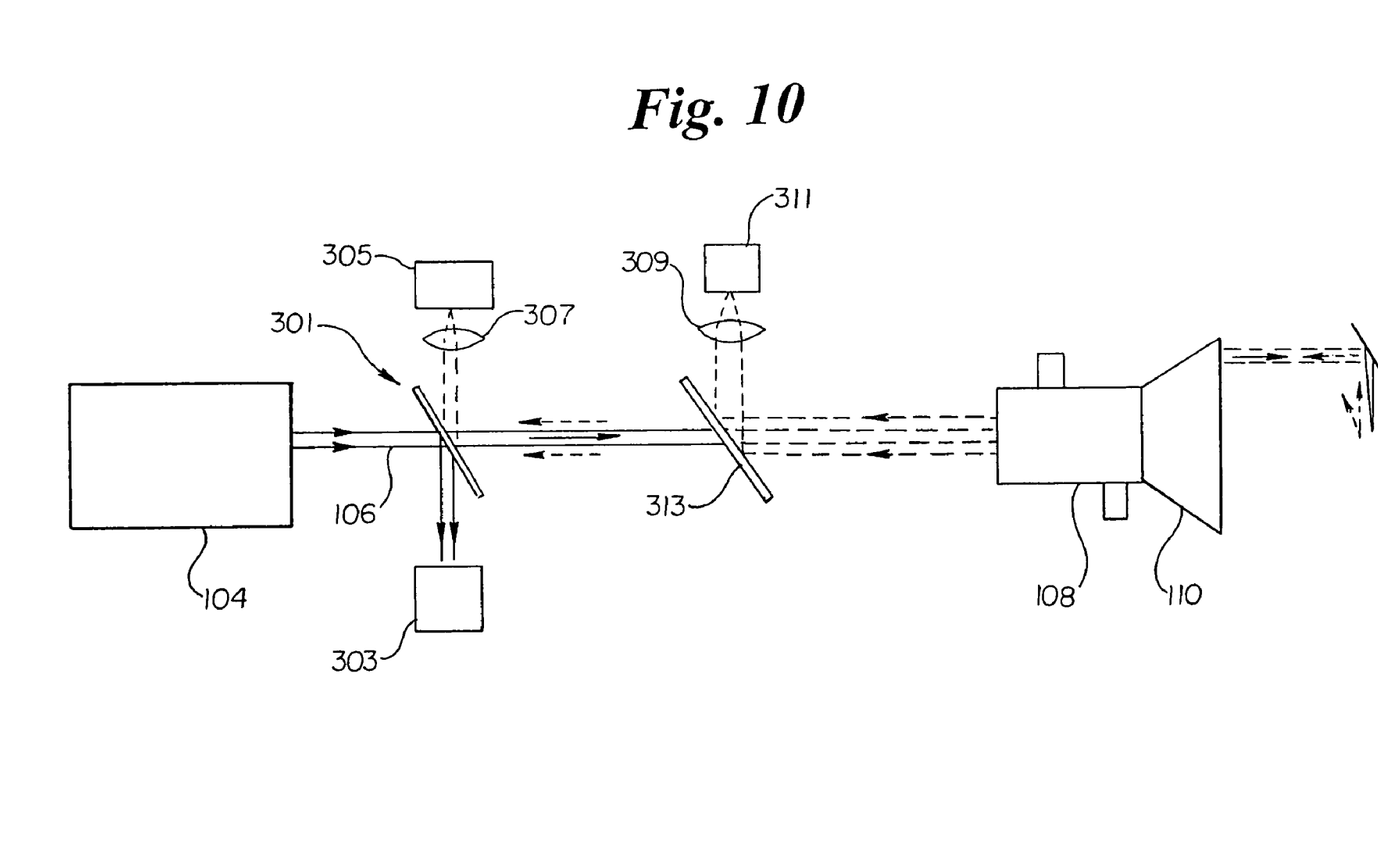
FIG. 10 is a schematic illustration of a portion of an inventive laser scanning system.

FIG. 10 shows a schematic illustration of a system for monitoring the radiation emitted and reflected radiation between the laser and the scanning galvanometer. Beam 106 is emitted from laser 102 and split using beam splitter 301. A portion of the beam, desirably no more than 5%, is sampled by detector 303 to monitor the wavelength of the emitted radiation. Lens 307 is used to focus the reflected laser radiation which is sampled by detector 305. A third lens 309 and detector 311 are present for monitoring purposes as well. Dichroic mirror 313 reflects the emitted radiation only.

Optionally, a gas stream may be directed along the axis of the tube. The gas may be a stream of air or nitrogen or an inert gas such as helium, argon, neon, krypton, xenon which is directed along the outside and inside of the tube to carry away metal vapor and particles from the site of the cutting. In addition to preventing undesirable metal deposits on the tube, this also helps in preventing damage to the optical elements, for example, the mirrors, that are used. The use of a gas jet may also serve to cool the tube and prevent overheating.

A jet of oxygen may also be directed at the tube along its axis to assist in the cutting process. The laser beam acts as an ignition source and controls the reaction of the oxygen with the metal.

Optionally, the method may further comprise the step of polishing the stent after the cutting step. Any standard polishing step may be used.

The inventive techniques disclosed herein may also be used in the manufacture of other medical devices as well including vena cava filters and various catheter parts. By way of example, where catheter tubes having sidewalls with openings therethrough are desired, the inventive techniques may be used to provide the openings in the sidewalls of the catheter tubes. Yet another example where the inventive technique may be used is in providing openings in a bumper for a catheter. Such a bumper is disclosed in U.S. application Ser. No. 09/681,462. Another application is in the manufacture of skids as disclosed in U.S. application Ser. No. 09/682,013.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction.

This completes the description of the embodiments of the invention. Those skilled in the art may recognize other equivalents to the specific embodiment described herein which equivalents are intended to be encompassed by the claims attached hereto.

The invention claimed is:

1. A method of manufacturing a medical device from a workpiece, comprising:
   generating a beam of radiation from a radiation source; and
   directing the radiation beam onto the workpiece by scanning the radiation beam with a scanning galvanometer to redirect the radiation beam in a desired manner within a planar scan area so that a prescribed pattern is cut in the workpiece, wherein a conical mirror is positioned along an optical path between the radiation source and the workpiece, the conical mirror having an apex with an aperture through which the workpiece passes.

2. The method of claim 1 wherein the radiation beam is scanned within the planar scan area throughout which the beam is incident at a 90° angle.

3. The method of claim 1 wherein the workpiece is a tubular workpiece.

4. The method of claim 3 wherein the planar scan area is perpendicular to a longitudinal axis of the tubular workpiece.

5. The method of claim 1 wherein the scanning galvanometer comprises a first pivotable scanning mirror pivotable about a first axis and a second pivotable scanning mirror pivotable about a second axis, wherein the first and second axes are orthogonal to one another.

6. The method of claim 1 further comprising the step of positioning at least one optical element along an optical path between the radiation source and the workpiece.

7. The method of claim 6 wherein the optical element comprises a flat field telecentric lens.

8. The method of claim 1 wherein the directing step includes the step of focusing the beam in a flat focal plane prior to impinging on the workpiece.

9. The method of claim 1 wherein the workpiece comprises a biocompatible material.

10. The method of claim 9 wherein said biocompatible material is stainless steel.

11. The method of claim 1 wherein the medical device is a stent.

12. The method of claim 1 wherein the medical device is a catheter.

13. The method of claim 1 wherein the workpiece is translated along its longitudinal axis during the step of directing the radiation beam.

14. The method of claim 3 wherein the tubular workpiece is rotated about its longitudinal axis during the step of directing the radiation beam.

15. The method of claim 1 wherein the radiation beam is a laser beam.

16. The method of claim 15 wherein the laser beam is a pulsed laser beam.

17. The method of claim 1 wherein the workpiece is cut by scanning the radiation over a common path a plurality of times, wherein each subsequent scan over the common path removes additional material from the workpiece.

* * * * *